United States Patent [19]

Dykstra

[11] Patent Number: 4,769,009
[45] Date of Patent: Sep. 6, 1988

[54] APPARATUS FOR DISPLACING A PISTON IN A CHAMBER HAVING A TORQUE RESISTOR

[75] Inventor: Raymond C. Dykstra, Boulder, Colo.

[73] Assignee: Cobe Laboratories, Inc., Lakewood, Colo.

[21] Appl. No.: 917,789

[22] Filed: Oct. 10, 1986

[51] Int. Cl.⁴ .............................................. A61M 37/00
[52] U.S. Cl. ............................ 604/155; 128/DIG. 1; 128/12; 128/655; 222/390
[58] Field of Search ................ 604/154, 155; 128/DIG. 1, DIG. 12, 655; 222/41, 390

[56] References Cited

U.S. PATENT DOCUMENTS

| | | | |
|---|---|---|---|
| 3,156,236 | 11/1964 | Williamson | 128/655 |
| 4,465,474 | 8/1984 | Mardorf et al. | 604/154 |
| 4,519,258 | 5/1985 | Jakubowicz | 128/DIG. 1 |
| 4,624,658 | 11/1986 | Mardorf et al. | 128/DIG. 1 |

Primary Examiner—C. Fred Rosenbaum
Assistant Examiner—J. L. Kruter

[57] ABSTRACT

Apparatus for displacing a piston in a chamber comprising a support member, a motor including a housing and a driving member that rotates relative to the housing and a driving axis, the driving member being rotatably mounted with respect to the support member, a torque resistor between the motor housing and the support limiting relative rotation between the two except when the torque between the two exceeds a predetermined amount, a piston driver including a driven portion threadedly connected to the driving member and a displacement portion that is axially displaced in response to relative rotation between the driving member and the driven portion, and a housing rotation detector to detect when the housing rotates relative to the support, indicating resistance to axial movement of the piston driver.

11 Claims, 2 Drawing Sheets

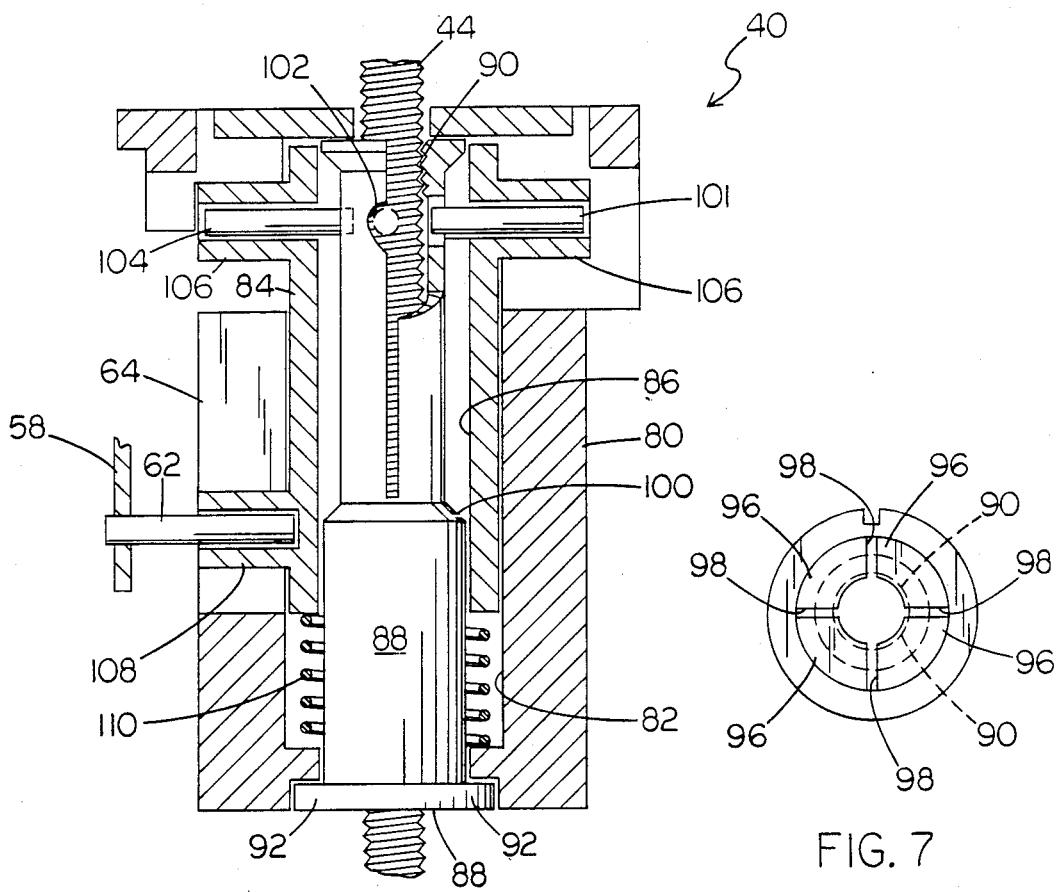
FIG. 3
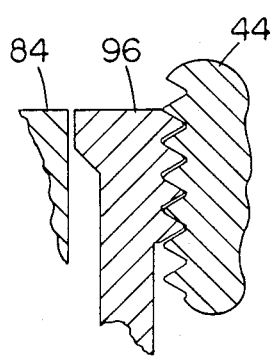
FIG. 4
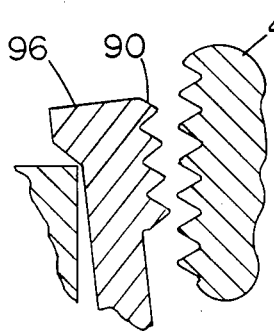
FIG. 5
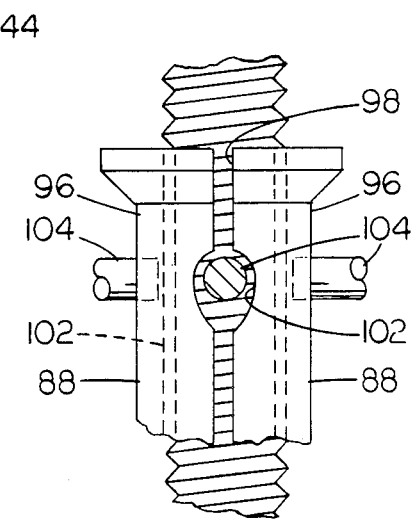
FIG. 6
FIG. 7

APPARATUS FOR DISPLACING A PISTON IN A CHAMBER HAVING A TORQUE RESISTOR

FIELD OF THE INVENTION

The invention relates to apparatus for displacing a piston in a chamber, e.g., a piston in a syringe used to very slowly pump heparin or other drugs into a blood flow line of a medical device.

BACKGROUND OF THE INVENTION

Syringes are often used to pump heparin or other drugs to a blood flow line of a medical device at very low flow rates, e.g., ½ to 6 milliliters per hour, by driving the plunger with a stepper motor. As syringes of different dimensions may be used on the same machine model, it can be difficult to correlate the position of the plunger driving mechanism with the end of travel of the plunger, something desired to accurately determine when the syringe has been emptied and to shut off the stepper motor driving it. Some prior art heparin pumps employ clutches that slip when the plunger has reached the end of travel, to prevent damage to machine parts.

SUMMARY OF THE INVENTION

I have discovered that the end of travel of a piston in a chamber can be advantageously detected by driving the piston using a motor that is rotatably mounted with respect to the motor's driving member on a support and has a motor housing mounted for rotation with respect to the support when the torque of the driving member exceeds a predetermined value. A housing rotation detector is used to detect when the housing rotates relative to the support, indicating resistance to movement of the piston associated with the end of its travel in a chamber.

In preferred embodiments the driving member of the motor is a threaded shaft, and the piston is driven with a member that has female threads that mate with the threaded shaft; the female threads are located on a plurality of separable segments that can be radially displaced into and out of engagement with the threaded shaft, to permit the piston driver to be axially displaced without rotation of the driving member, to reset the piston driver; there is a disengagement button operatively connected to the separable segments to separate them to disengage the threaded shaft; the segments are separated by opposing cam surfaces that are inclined with respect to the threaded drive shaft axis (the "driving axis"), and there is an actuator that is slidably mounted along the driving axis, and includes separation pins located between opposing cam surfaces, the actuator being operatively connected to the button; a torsion spring having coils around the driving axis and one end connected to the housing and another end connected to the support is used to limit rotation of the housing with respect to the support; the housing carries a cam member with a surface that is inclined with respect to an arc of travel of it about the driving axis, and the housing rotation detector includes an electrical switch having an actuation member that is displaced by the cam member during relative rotation of the two; and the piston is connected to a plunger and located in a syringe, and there is means to detachably engage the syringe on the front of the faceplate.

Other advantages and features of the invention will be apparent from the following description of a preferred embodiment thereof and from the claims.

DESCRIPTION OF THE PREFERRED EMBODIMENT

The preferred embodiment will now be described.

Drawings

FIG. 3 is a vertical sectional view, taken at 3—3 of FIG. 2, of a portion of a piston driver mechanism of the FIG. 1 apparatus.

FIGS. 4 and 5 are enlarged partial vertical sectional views showing the threaded connection between a drive shaft and a piston driver in engaged and disengaged positions.

FIG. 6 is a partial elevation, partially broken away, of the drive shaft and mating piston driver portions shown in FIGS. 4 and 5.

FIG. 7 is a plan view of a latch member of the FIG. 3 piston driver mechanism.

Structure

Figure 1:
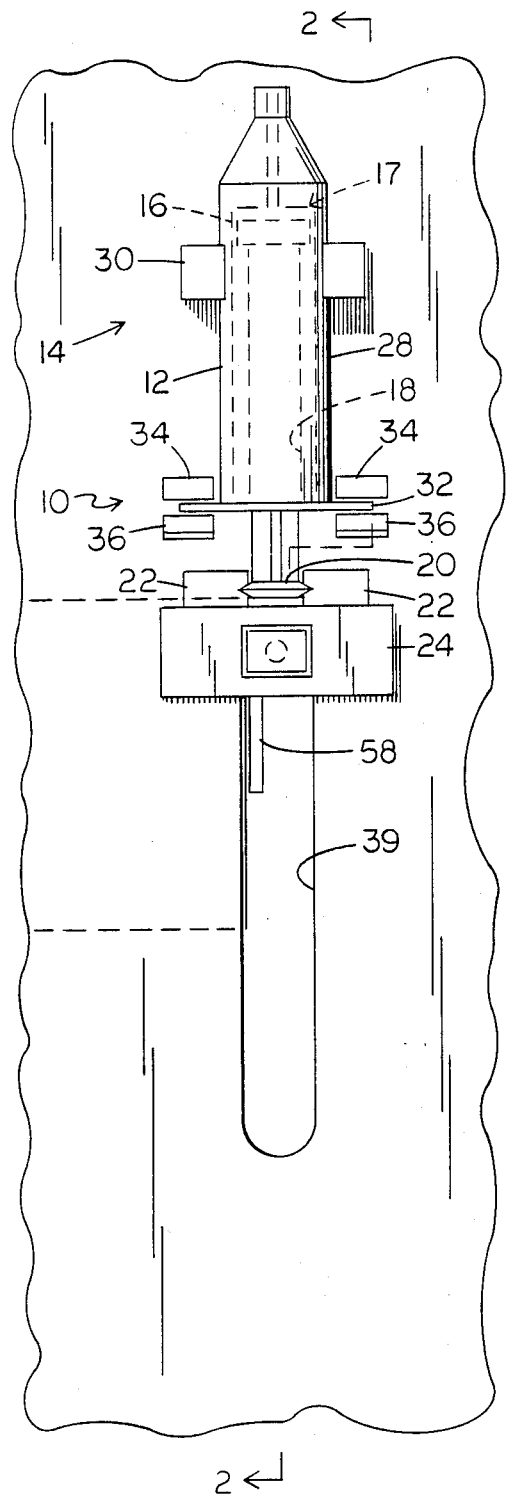
FIG. 1 is a diagrammatic elevation of a syringe pump according to the invention.
Figure 2:
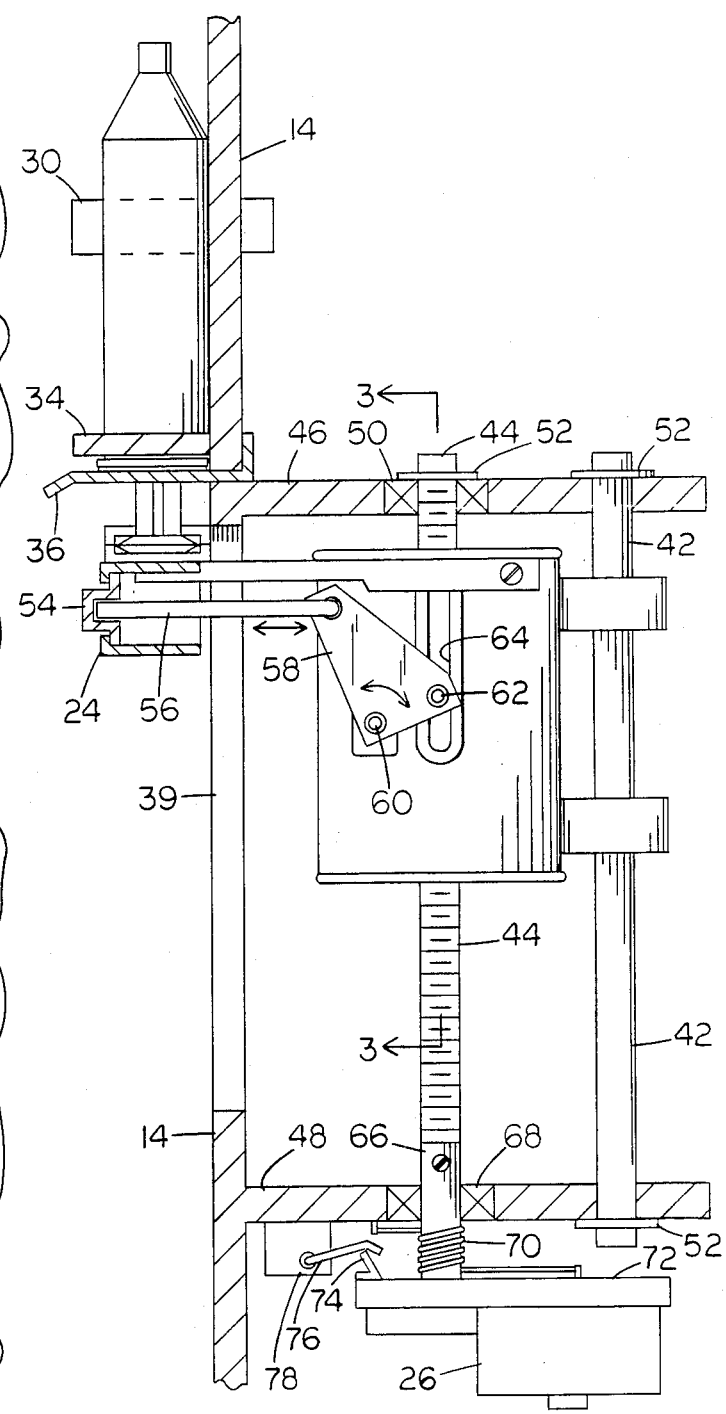
FIG. 2 is a diagrammatic vertical sectional view, taken at 2—2 of FIG. 1, of the FIG. 1 apparatus.

Referring to FIGS. 1, 2, there is shown heparin pump 10, including syringe 12 mounted on the front of faceplate 14 of a dialysate preparation and supply machine. Syringe 12 includes piston 16 located in the upper end of chamber 17 and connected to plunger 18. Base 20 of plunger 18 is engaged between openable jaws 22 mounted on the upper surface of plunger engager 24, driven by a stepper motor 26 behind faceplate 14. Body 28 of syringe 12 is engaged by clamp arms 30, and wings 32 of syringe 12 are retained between horizontal arms 34 and horizontal resilient clips 36 thereunder.

Plunger engager 24 is fixedly connected by horizontal arm 38 to piston driver 40, which is slidably mounted for axially movement along guide shaft 42 and is driven (via female threads on internal members) along threaded drive shaft 44 connected to stepper motor 26. Horizontal arm 38 passes through slot 39 of faceplate 14. Plunger engager 24 includes release button 54, connected by L-shaped rod 56 to triangular plate 58, pivotally mounted to driver 40 about pivot 60. Pin 62, passing through plate 58, is slidably mounted in slot 64 to disengage the threads of piston driver 40 from threaded shaft 44 by the mechanism shown in FIGS. 3–7, when button 54 is depressed.

The top of drive shaft 44 is rotatably mounted in bearing 50 in plate 46 and retained by a clip 52. The bottom of drive shaft 44 is connected to stepper motor drive extension 66, which is rotatably mounted in bearing 68 in horizontal plate 48. Guide shaft 42 is mounted on horizontal plates 46, 48 and retained by clips 52.

Torsion spring 70 has one end retained by plate 48, and another end retained in housing 72 of motor 26, resisting rotation of housing 72. Cam member 74 is carried by housing 72. Within the arc of the path of travel of cam member 74 is actuation member 76 of switch 78, to detect rotation of housing 72. Although faceplate 14, horizontal plate 46, and horizontal plate 48 are shown diagrammatically as an integral support member, they are made up of separate parts secured to each other, as are some of the other components shown in the drawings.

Referring to FIGS. 3-7, there is shown the releasable threaded connection mechanism of piston driver 40. Cylindrically-shaped housing 80 has a cylindrical passage 82 in which is located actuator 84, capable of slight vertical movement. Actuator 84 has an inner cylindrical passage 86 in which is located Delrin (acetal plastic) latch member 88 having threads 90 for releasably engaging the threads of threaded shaft 44. Latch member 88 includes lower flange 92, cylindrical base 94 thereabove, and four segmented extensions 96 thereabove, the upper ends of which include threads 90. Slots 98 between segments 96 begin above base 94 at enlarged circular openings 100 (to increase the separability of the segments) and expand at oblong-shaped openings 102, which receive the ends of radially oriented pins 104 carried in four cross members 106 at the top of actuator 84. Actuator 84 also has a single cross member 108 within slot 64 and containing pin 62. Below actuator 84 is compression spring 110 pushing actuator 84 upward.

Operation

In operation, syringe 12 is mounted on the front of the dialysate preparation and supply machine by engaging body 28 between clamp arms 30, by retaining wings 32 between arms 34 and clips 36, and by engaging base 20 of plunger 18 between jaws 22 on top of plunger engager 24. Because syringe 12 is initially filled with heparin, plunger 18 extends from the bottom of body 28 by a larger distance than that shown in FIG. 1, and plunger engager 24 must first be moved to a lower position by depressing button 54 to disengage female threads 90 from threaded drive shaft 44 (FIG. 5).

Depressing button 54 causes rod 56 to be horizontally displaced and plate 58 to pivot, lowering pin 62, actuator 84 and the four pins 104 carried by actuator 84. As the four pins 104 move downward within in oblong-shaped openings 102, segments 96 separate from the threaded engagement position shown in FIG. 4 to the disengagement shown in FIG. 5. As the top of actuator 84 moves downward, it moves from the FIG. 4 position, in which it interferes with separating of segmented extensions 96, to the FIG. 5 position adjacent to narrower portions of segmented extensions 96, permitting their separation. The disengagement of threads permits piston driver 40 to be moved axially along drive shaft 44 without rotation of it.

With plunger engager 24 now in the proper position, base 20 of plunger 18 is fitted within opposing jaws 22, and heparin is slowly pumped from syringe 12 by rotation of drive shaft 44, which rotation is converted to axial motion of piston driver 40 via threads 90. When piston 16 reaches the end of travel within chamber 17, it is restrained from axial movement, thereby increasing the torque between drive shaft 44 and motor housing 72. As the torque increases, motor housing 72 rotates (the torque of spring 70 similarly increasing), and actuation member 76 is triggered when it is hit by cam member 74. This causes the stepper motor to be turned off, to prevent damage to the equipment, and is used to provide an indication to the operator that the heparin syringe is empty. Heparin pump 10 can be used with different sized syringes 12 having different ends of travel for the pistons, owing to the rotatable mounting of motor 26 by its drive extension 66 and the torque-sensing provided by torsion spring 70 and switch 78.

OTHER EMBODIMENTS

Other embodiments of the invention are within the scope of the following claims.

What is claimed is:

1. Apparatus for displacing a piston in a chamber comprising
    a support member,
    a motor including a housing and a driving member that is mounted within said housing and rotates relative to said housing about a driving axis, said driving member being rotatably mounted with respect to said support member, said housing being mounted on said support member, for limited relative rotation therewith,
    a torque resistor means connected between said motor housing and said support member so as to limit relative rotation between the two except when the torque between the two exceeds a predetermined amount,
    a piston driver including a driven portion threadedly connected to said driving member and a displacement portion that is axially displaced in response to relative rotation between said driving member and said driven portion, and
    a housing rotation detector means to detect when said housing rotates relative to said support member, indicating resistance to axial movement of said piston driver.

2. The apparatus of claim 1 wherein said driving member comprises a threaded shaft, and said driven portion comprises female threads mating with said threaded shaft.

3. The apparatus of claim 2 wherein said female threads are on a plurality of separable segments that can be radially displaced into and out of engagement with said threaded shaft, to permit said piston driver to be axially displaced without rotation of said driving member, to reset the position of said piston driver.

4. The apparatus of claim 3 further comprising a disengagement button operatively connected to said separable segments to separate them to disengage said threaded shaft.

5. The apparatus of claim 4 wherein said segments have cam surfaces that are inclined with respect to said driving axis and further comprising an actuator that surrounds said segments, is slidably mounted along said driving axis and comprises separation members mounted to bias said members at said surfaces during movement along said axis, said actuator being operatively connected to said button so as to be axially displaced and to separate said segments when said button is depressed.

6. The apparatus of claim 5 wherein said cam surfaces are opposing cam surfaces on adjacent segments, and said separation members are pins carried by said actuator 7. The apparatus of claim 5 wherein the top of said actuator interferes with separation of said segments when said button is not depressed, and moves into a position that does not interfere with separation of said segments when said button is depressed.

8. The apparatus of claim 1 wherein said torque resistor means comprises a torsion spring having coils around said driving axis and one end connected to said housing and another end connected to said support.

9. The apparatus of claim 1 wherein said housing carries a cam member with a cam surface that is inclined with respect to an arc of travel about said driving axis, and said housing rotation detector means comprises an electrical switch having an actuation member that is positioned along said arc of travel so as to be displaced by said cam surface during relative rotation of said actuation member and cam surface about said arc.

10. The apparatus of claim 1 wherein said support member includes a faceplate, and said piston is connected to a plunger and located in a body of a syringe, and further comprising body engagement means to detachably engage said body in front of said faceplate, and wherein said piston driver comprises a plunger engagement mechanism that detachably engages said plunger in front of said faceplate.

11. The apparatus of claim 2 further comprising a guide shaft mounted on said support member parallel to said driving axis, said piston driver being slidably mounted on said guide shaft.

* * * * *